US012781174B2

(12) United States Patent
Nanba et al.

(10) Patent No.: US 12,781,174 B2
(45) Date of Patent: Nov. 3, 2026

(54) ASEPTIC SAMPLING APPARATUS AND ASEPTIC SAMPLING METHOD

(71) Applicant: Hitachi High-Tech Corporation, Tokyo (JP)

(72) Inventors: Masaru Nanba, Tokyo (JP); Keisuke Shibuya, Tokyo (JP); Kenichiro Oka, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 657 days.

(21) Appl. No.: 18/267,523

(22) PCT Filed: Jan. 26, 2021

(86) PCT No.: PCT/JP2021/002564

§ 371 (c)(1),
(2) Date: Jun. 15, 2023

(87) PCT Pub. No.: WO2022/162722

PCT Pub. Date: Aug. 4, 2022

(65) Prior Publication Data

US 2024/0052283 A1 Feb. 15, 2024

(51) Int. Cl.

*C12M 1/00* (2006.01)
*C12M 1/26* (2006.01)
*C12M 1/34* (2006.01)

(52) U.S. Cl.

CPC ............ *C12M 33/12* (2013.01); *C12M 41/40* (2013.01)

(58) Field of Classification Search

None

See application file for complete search history.

(56) References Cited

U.S. PATENT DOCUMENTS

2013/0059339 A1 3/2013 Karerangabo et al.
2019/0250073 A1 8/2019 Makino et al.
2020/0063106 A1* 2/2020 Shibuya ................ C12M 41/12

FOREIGN PATENT DOCUMENTS

JP 60-227697 A 11/1985
JP 64-80279 A 3/1989
JP 5-176752 A 7/1993
JP 3137396 B2 2/2001
JP 2013-526269 A 6/2013
JP 2016-208864 A 12/2016
JP 2019-136005 A 8/2019
WO WO 99/30835 * 6/1999

OTHER PUBLICATIONS

International Search Report (PCT/ISA/210) issued in PCT Application No. PCT/JP2021/002564 dated Mar. 2, 2021 with English translation (seven (7) pages).
Japanese-language Written Opinion (PCT/ISA/237) issued in PCT Application No. PCT/JP2021/002564 dated Mar. 2, 2021 (five (5) pages).

* cited by examiner

*Primary Examiner* — Jyoti Mutreja
(74) *Attorney, Agent, or Firm* — Crowell & Moring LLP

(57) ABSTRACT

The aseptic sampling apparatus according to the present invention includes: a sampling channel for pulling out a culture solution in a culture tank to supply the same to an analytical unit; and a pressure-applying unit for applying a pressure to the inside of the sampling channel. The pressure-applying unit controls the flow pressure or fluid flow rate of a fluid in the sampling channel such that a pressure gradient toward the outlet-side open end nozzle of the sampling channel is not less than 1 kPa/m.

13 Claims, 3 Drawing Sheets

[FIG. 1]
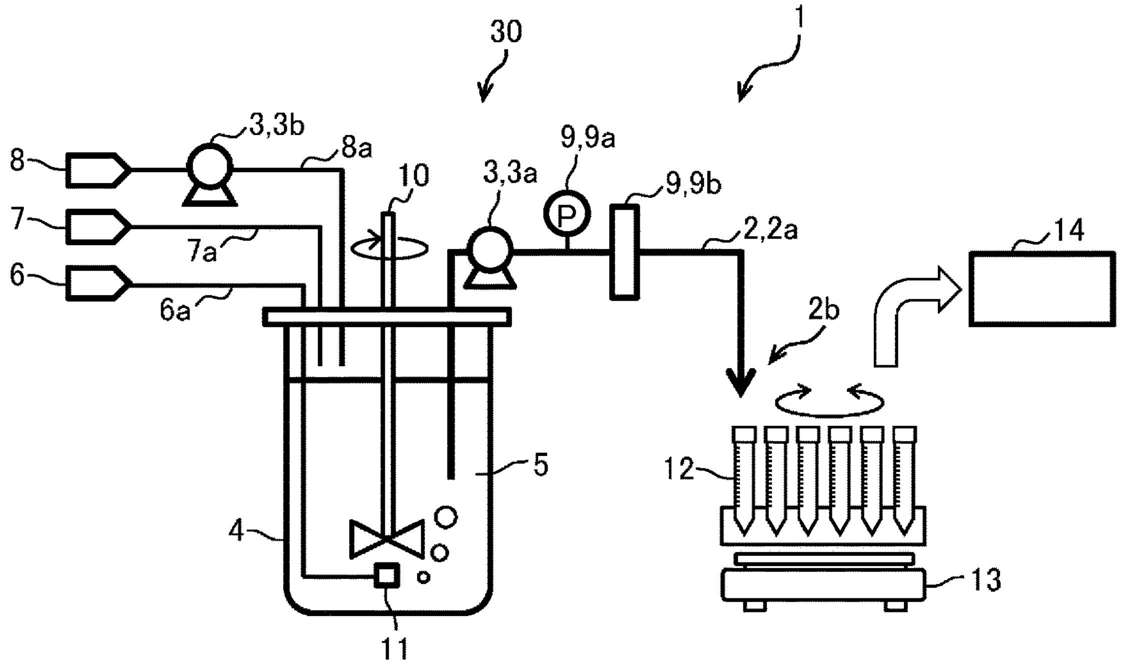
[FIG. 2]
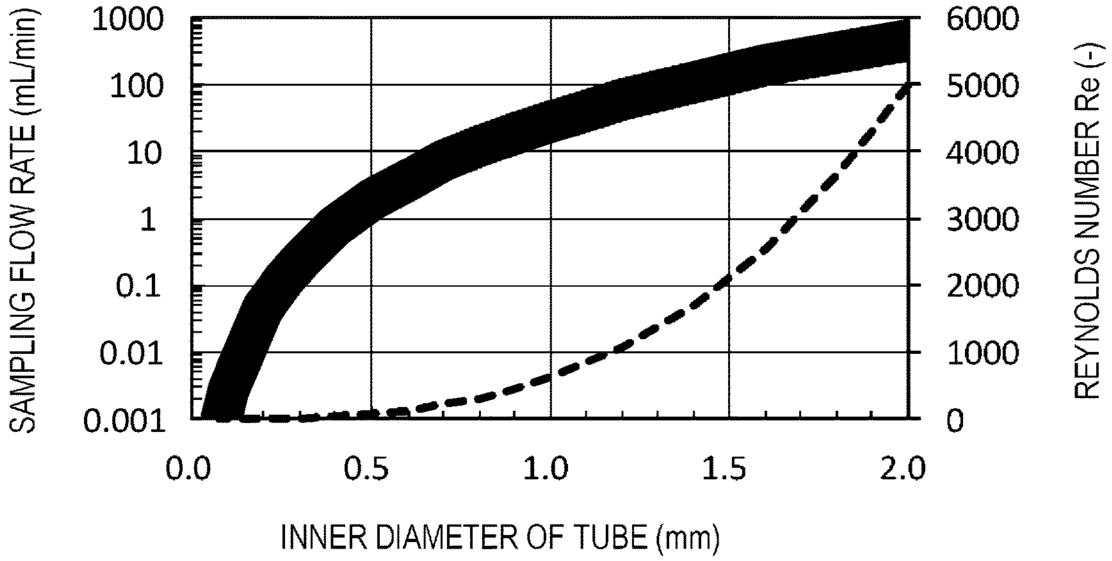

[FIG. 3]
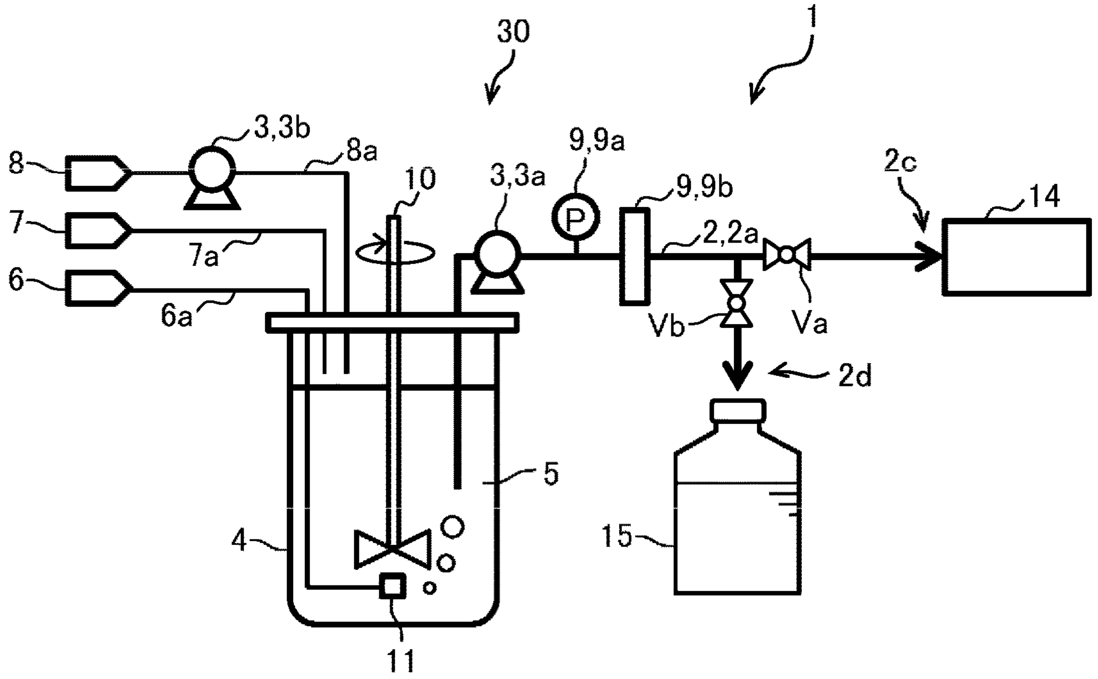

[FIG. 4]
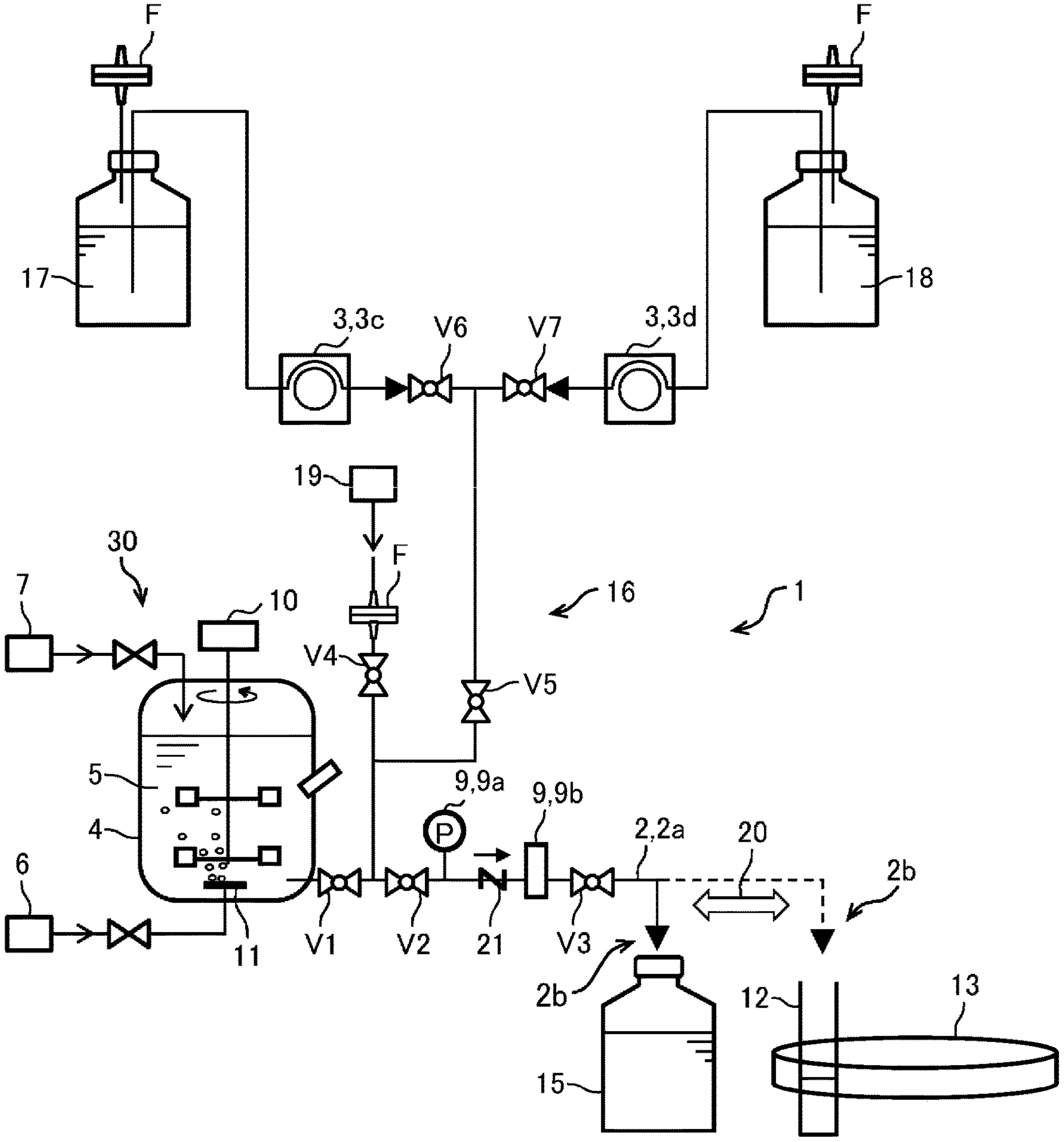

ASEPTIC SAMPLING APPARATUS AND ASEPTIC SAMPLING METHOD

TECHNICAL FIELD

The present invention relates to an aseptic sampling apparatus and an aseptic sampling method.

BACKGROUND ART

In technical fields such as regenerative medicine and biopharmaceutical manufacturing, where cells are required to be cultured, a cell culture apparatus performing long-term culture while maintaining aseptic states has been developed. In many cases, in cell culture using the cell culture apparatus, subject cells are cultured under predetermined conditions to induce differentiation into target cells or to produce target macromolecular proteins. In addition, in the cell culture using the cell culture apparatus, the culture is generally performed in a culture tank filled with a medium optimized for the subject cells while ventilation and stirring are performed.

In the cell culture using the cell culture apparatus, a state of the culture liquid in the culture tank during the culture is measured. Online measurement of the state of the culture liquid is widely performed by using various electrodes and sensors according to various parameters such as temperature, pH, dissolved oxygen (DO) concentration, and dissolved carbon dioxide ($DCO_2$) concentration.

In addition, in the cell culture using the cell culture apparatus, a portion of the culture liquid is aseptically sampled and measured with various measurement instruments during culture if necessary. In many cases, the measurement is often performed outside the culture tank using the sampled culture liquid on medium components involved in cell metabolism, such as amino acids of glutamine and the like, glucose, lactate, ammonia, and produced proteins (antibodies or the like).

In many cases, the above-described measurements are performed on specific proteins. For the measurement of the specific proteins, in addition to HPLC (high performance liquid chromatography), various analysis methods of ELISA (enzyme-linked immunosorbent assay) including a sensing unit retaining an antibody against or a substance with affinity for a target product, ECL (electrochemiluminescence), SPR (surface plasmon resonance), and the like are used.

In addition, the above-described measurements may be performed on variants of macromolecular proteins. In addition to LC/MS (liquid chromatograph mass spectrometer), isoelectric-point electrophoresis, capillary electrophoresis, and the like are used for the measurement of the variants of macromolecular proteins.

Furthermore, the above-described measurements may be performed to analyze the state of cell differentiation using a staining agent, the counting of the number of cells determined to be alive or dead, viability, a cell diameter, a cell morphology, and the like of the cultured cells. The sampling operation of directly extracting the cells from the culture tank is required to perform these analyzes.

In particular, in applications for regenerative medicine, it is necessary to grasp the differentiated state of the cultured cells and the like, and it is necessary to extract the culture liquid containing cells into a non-aseptic space while maintaining asepticity of the cell culture apparatus. In the sampling, an aseptic operation is required to avoid contamination due to various germs. In addition, a sampling apparatus is required to have a structure of preventing microorganisms from invading from the outside and a structure of greatly avoiding retention of the culture liquid in the device.

In the related art, the sampling operation of the culture liquid from the inside of the culture tank has been performed manually by opening the valve from a tube for sampling provided in the culture tank and collecting the required amount. A sampling port of the tube is arranged in an aseptic space such as a glove box, and sterilization needs to be performed with a steam, a flame, a disinfectant, or the like before and after sampling the culture liquid, which requires manual work. It is noted that, in a culture plant where the culture tank and a pipe are made of stainless steel, after a sampling piping system is steam sterilized, the culture liquid containing cells is sampled, and after that, steam sterilizing is performed again, washing is performed with aseptic water, and remaining liquid in the pipe is discarded with aseptic air. Although automation of the steps is possible, it takes a lot of time before and after the sampling due to the execution of the plurality of steps, and it is difficult to shorten a sampling interval.

Under such circumstances, for example, a sampling apparatus described in PTL 1 has been proposed. The sampling apparatus is configured with a sampling nozzle, an automatic pinch valve for suctioning a sample leading to the sampling nozzle, a sample suctioning tube pump, an automatic pinch valve connecting or separately connecting the aseptic air feeding pipe and the steam feeding pipe, an automatic pinch valve connecting or separately connecting the chemical feeding pipe and the aseptic water feeding pipe, and a pipe connecting the above-described elements. In the apparatus, the opening and closing of each automatic pinch valve and the operation of the sample suctioning tube pump are controlled by a control device and are performed by freely combining operations of sterilization, flushing, steam sterilization, chemical sterilization, and washing and sampling stored in advance in the control device. According to PTL 1, it is possible to uniformly sample a solid-liquid phase with the apparatus, and it is described that sterilization and washing can be performed efficiently when the sample contains perishable organic matters.

CITATION LIST

Patent Literature

PTL 1: JP3137396B

SUMMARY OF INVENTION

Technical Problem

In the living cell culture, the culture is well controlled in a culture status where the culture status changes from moment to moment, and the concentration of the living cells is low at the beginning of the culture, but in some cases, as the concentration of the living cells increases, there may be a status where a target culture environment cannot be maintained. In order to maintain the culture environment suitable for culturing the living cells, it is necessary to perform appropriate culture control as the living cells are cultured.

When the culture method is perfusion culture, the culture liquid containing cells is extracted from the culture tank, the cells are separated by using centrifugal separation or a tangential flow filtration device (TFF) including a hollow fiber membrane filter, and the separated cells are returned to the culture tank and only the culture liquid is discharged out of the system. In the perfusion culture, at the same time, the same amount of a fresh medium as the discharged culture liquid is supplied to perform long-term continuous culture. Therefore, in the case of the perfusion culture, since the separated cells are returned to the culture tank, the medium components and the metabolic components of the cells can be measured by using the discharged culture liquid, but the cells themselves cannot be analyzed.

The sampling apparatus described in PTL 1 described above can make it possible to sample cells from the culture tank even in the case of perfusion culture. However, the sampling apparatus requires the operations of various apparatuses for sampling, and the configuration is complicated and expensive.

An object of the invention is to provide an aseptic sampling apparatus and an aseptic sampling method with a simple configuration and at low cost.

Solution to Problem

An aseptic sampling apparatus according to the invention solving the above problems includes: a sampling channel extracting a culture liquid from a culture tank to be tested in an analysis device and a pressure applying device applying pressure to the sampling channel, in which the pressure applying device controls a flow pressure or a liquid flow speed of a fluid in the sampling channel so that a pressure gradient toward an open-end nozzle on an outlet side of the sampling channel is 1 kPa/m or more.

Advantageous Effects of Invention

According to the invention, an aseptic sampling apparatus and an aseptic sampling method with a simple configuration and at low cost can be provided. Problems, configurations, and effects other than those described above will be clarified by the following description of the embodiments.

BRIEF DESCRIPTION OF DRAWINGS

FIG. 1 is a schematic diagram illustrating an overall configuration of a cell culture apparatus 30 including an aseptic sampling apparatus 1 according to a first embodiment.

FIG. 2 is a graph illustrating an example of selection of an inner diameter of a tube 2*a* for sampling and a flow rate. In the figure, a horizontal axis is an inner diameter (mm) of the tube 2*a*, a left vertical axis is a sampling flow rate (mL/min), and a right vertical axis is a Reynolds number Re (–).

FIG. 3 is a schematic diagram illustrating an overall configuration of a cell culture apparatus 30 including an aseptic sampling apparatus 1 according to a second embodiment.

FIG. 4 is a schematic diagram illustrating an overall configuration of a cell culture apparatus 30 including an aseptic sampling apparatus 1 according to a third embodiment.

DESCRIPTION OF EMBODIMENTS

Hereinafter, embodiments of an aseptic sampling apparatus and an aseptic sampling method according to the invention will be described in detail with reference to the drawings as appropriate.

[Aseptic Sampling Apparatus 1]

First Embodiment

FIG. 1 is a schematic diagram illustrating an overall configuration of a cell culture apparatus 30 including an aseptic sampling apparatus 1 according to a first embodiment.

As illustrated in FIG. 1, the aseptic sampling apparatus 1 according to the present embodiment is connected to a culture tank 4 of the cell culture apparatus 30. The aseptic sampling apparatus 1 is preferably used for online monitoring of culture states of cells in the cell culture apparatus 30.

The cell culture apparatus 30 is applied when culturing animal-derived or human-derived cells producing useful substances that are main raw materials of biopharmaceuticals, health foods, and the like. In addition, the cell culture apparatus 30 is applied when culturing stem cells having multipotency capable of differentiating into various cells/organs such as skin, nerves, bones, and blood vessels and an ability to proliferate almost infinitely in regenerative medicine applications.

The cells cultured in the cell culture apparatus 30 include, for example, Chinese hamster ovary cells (CHO cells), baby hamster kidney cells, mouse myeloma cells, and the like which are generally used as cells for producing useful substances, but are not limited thereto.

When the cells cultured in the cell culture apparatus 30 are adherent cells, stirring culture can be performed by attaching the cells to the carriers such as the microcarriers and suspending the cells.

The stem cells include, for example, human mesenchymal stem cells (hMSCs), iPS cells (induced pluripotent stem cells), human ES cells (embryonic stem cells), and the like, but are not limited thereto. It is noted that the stem cells can be induced to differentiate into target tissues or organs after being proliferated in the culture tank 4.

The useful substances described above include, for example, macromolecular proteins, but are not limited thereto. The macromolecular proteins include, for example, physiologically active substances, and particularly, antibodies. The antibodies include, for example, monoclonal antibodies, polyclonal antibodies, humanized antibodies, human antibodies, immunoglobulins, and the like. In addition, the physiologically active substances are not limited to the antibodies, but include tissue-type plasminogen activators used as a thrombolytic agent, biopharmaceuticals such as erythropoietin and interferon, and other industrially useful proteins, and also include proteins obtained by binding pigments such as carotenoids such as β-carotene or astaxanthin and chlorophyll or bacteriochlorophyll. Furthermore, the physiologically active substances also include phycobilin proteins such as phycocyanin which are used for coloring foods and cosmetics.

The medium used for the culture is not particularly limited, and any medium in the related art can be used as long as the medium is effective for proliferation of the cells to be cultured and production of the useful substances.

Then, in the present embodiment, as illustrated in FIG. 1, the aseptic sampling apparatus 1 includes a sampling channel 2 and a pressure applying device 3.

The sampling channel 2 is a tube 2*a*, that is, a hollow member, from which the culture liquid 5 in the culture tank 4 is extracted to be tested in an analysis device 14. It is noted that the culture liquid 5 is a solution containing the cells cultured in the liquid medium.

The pressure applying device 3 is a device applying pressure to the inside of the sampling channel 2. The pressure applying device 3 is provided at any position between one end of the sampling channel 2 (the connection end with the culture tank 4) and the other end (an open-end nozzle 2*b* on an outlet side). The pressure applying device 3 is, for example, a liquid feeding pump 3*a*.

The aseptic sampling apparatus 1 controls a fluid in the sampling channel 2 by the pressure applying device 3 so that a pressure gradient toward the open-end nozzle 2*b* on the outlet side of the sampling channel 2 is 1 kPa/m or more. It is noted that, as the above-described fluid, in the first embodiment, for example, the culture liquid 5 can be exemplified. By doing so, the pressure gradient of the fluid in the sampling channel 2 is sufficiently high, so that various germs cannot invade from the open-end nozzle 2*b* on the outlet side. Even if the various germs invade from the open-end nozzle 2*b* for a moment, pressure resistance is generated by the fluid having the sufficient pressure gradient, and the various germs are swept out of the sampling channel 2 at a flow speed faster than a swimming speed of the various germs. Therefore, the aseptic sampling apparatus 1 can prevent contamination due to the various germs from the open-end nozzle 2*b* on the outlet side of the sampling channel 2. For this reason, the aseptic sampling apparatus 1 does not need to include various devices for sterilizing the open-end nozzle 2*b* with a steam, a flame, a disinfectant, or the like. Thus, according to the present embodiment, the aseptic sampling apparatus 1 with a simple configuration and at low cost can be implemented. Therefore, when the cell culture apparatus 30 includes the aseptic sampling apparatus 1, contamination can be prevented during the culture and the analysis with a simple configuration and at low cost.

It is noted that, it is preferable that the control of the pressure gradient is performed by controlling a flow pressure or a liquid flow speed by the pressure applying device 3. Moreover, it is preferable that the control of the pressure gradient is always performed while the fluid is present in the sampling channel 2.

Furthermore, as described above, since the aseptic sampling apparatus 1 controls a fluid in the sampling channel 2 by the pressure applying device 3 so that the pressure gradient toward the open-end nozzle 2*b* on the outlet side of the sampling channel 2 is 1 kPa/m or more, the cell culture apparatus 30 including the aseptic sampling apparatus 1 is capable of continuously sampling. In addition, the aseptic sampling apparatus 1 can also appropriately sample and analyze the culture liquid 5 containing the cells. As a result, the cell culture apparatus 30 including the aseptic sampling apparatus 1 can grasp the culture states of the cells and perform appropriate culture control. Furthermore, the aseptic sampling apparatus 1 can culture the target cells efficiently without wasting the culture liquid 5 by sampling a minimum amount of the culture liquid 5 required for analysis.

From the viewpoint of more reliable prevention of contamination, the pressure gradient is preferably 10 kPa/m or more. In addition, from the viewpoint of reducing an amount of the culture liquid 5 to be used, the pressure gradient is preferably 100 kPa/m or less, more preferably 30 kPa/m or less.

An inner diameter of the tube 2*a* is preferably 1.5 mm or less, more preferably 0.1 to 0.5 mm. By doing so, since the fluid flowing through the tube 2*a* is less likely to become turbulent and shear force is less likely to occur, damage to the cells in the culture liquid 5 during the sampling can be reduced. In addition, the flow rate of the fluid required to maintain the pressure gradient can be set to be small. It is noted that inner diameters of tubes other than the tube 2*a* (for example, tubes 6*a*, 7*a*, 8*a*, and the like described later) can be freely set.

It is preferable that the material of the tube 2*a* is, for example, fluororesin, polytetrafluoroethylene, tetrafluoroethylene/ethylene copolymer, tetrafluoroethylene/perfluoroalkyl vinyl ether copolymer, polyetheretherketone, or polyetheretherketone ketone. By doing so, the tube 2*a* having the inner diameter described above can be easily obtained.

It is preferable that the pressure applying device 3 is, for example, at least one of, a tube pump and a diaphragm pump. These pressure applying devices 3 can be used to apply pressure aseptically.

It is noted that, when discarding the liquid such as the culture liquid 5 remaining in the sampling channel 2 (tube 2*a*), at least one of an air pump for feeding aseptic air and an air compressor for feeding the aseptic air can be used as the pressure applying device 3. By doing so, pressure can be applied by the aseptic gas (aseptic air) as described in a third embodiment. It is noted that the feeding of the aseptic air by the air pump or the air compressor can be performed by providing the air pump or the air compressor with an aseptic filter F (refer to FIG. 4).

As illustrated in FIG. 1, the cell culture apparatus 30 includes, in addition to the culture tank 4 and the aseptic sampling apparatus 1, a submerged ventilation means 6, a liquid surface ventilation means 7, a medium supply means 8, and the like. The submerged ventilation means 6 plays a role of feeding the aseptic air into the culture liquid 5 in the culture tank 4. The submerged ventilation means 6 can be implemented by connecting, for example, the air pump or the air compressor including the aseptic filter (not illustrated in FIG. 1) to the culture tank 4 with the tube 6*a* and arranging the tube 6*a* in the culture liquid 5. In this case, it is preferable to provide a microbubble forming means such as a sparger 11 of allowing the bubbles to be small at a distal end of the tube 6*a* arranged in the culture liquid 5. By doing so, since the aseptic air becomes microbubbles, the efficiency of dissolving oxygen in the culture liquid 5 is increased. In addition, since the rising speed of the bubbles is slowed down and the impact caused by bursting of the bubbles on the liquid surface can be suppressed, the damage to the cells can be reduced.

The liquid surface ventilation means 7 plays a role of feeding the aseptic air to the liquid surface of the culture liquid 5 in the culture tank 4. The liquid surface ventilation means 7 can be implemented by connecting the air pump or the air compressor including the above-described aseptic filter (not illustrated in FIG. 1) to a gas phase portion of the culture tank 4 with the tube 7*a*.

The medium supply means 8 supplies a fresh medium in the same amount as the culture liquid 5 extracted from the sampling channel 2 into the culture tank 4 to maintain the amount of the culture liquid 5 in the culture tank 4 constant. It is noted that the fresh medium is a new medium containing no cells but containing nutrients required for cell culture. The medium supply means 8 is configured to include a medium supply tank (not illustrated) storing the fresh medium, a tube 8*a* connecting the medium supply tank and the culture tank 4, and a liquid feeding pump 3*b* which is a pressure applying device 3 installed on the tube 8*a*.

It is noted that the tubes 6*a*, 7*a*, and 8*a* can be made of the same material as the tube 2*a*.

Any of the submerged ventilation means 6, the liquid surface ventilation means 7 and the medium supply means 8 can be freely provided according to the culture method. It is noted that, in the present embodiment, since the predetermined amount of the culture liquid 5 is extracted, it is preferable to provide the medium supply means 8, and however, when the volume of the culture liquid 5 is large and the amount of the culture liquid 5 to be extracted is sufficiently small, the medium supply means 8 may not be provided. When the medium supply means 8 is not provided, the cell culture apparatus 30 provided with the aseptic sampling apparatus 1 can be provided with a simpler configuration and at lower cost.

Moreover, it is preferable that, as illustrated in FIG. 1, the aseptic sampling apparatus 1 includes a measurement device 9 measuring the flow pressure or the liquid flow speed in the sampling channel 2. It is preferable that the aseptic sampling apparatus 1 controls the pressure applying device 3 based on the measured value measured by the measurement device 9 and controls the flow pressure or the liquid flow speed so as to achieve the pressure gradient described above. By doing so, the aseptic sampling apparatus 1 can reliably control the pressure gradient described above.

As the measurement device 9 for measuring the flow pressure, for example, a pressure gauge 9*a* can be exemplified. As the measurement device 9 for measuring the liquid flow speed, for example, a liquid flow rate meter 9*b* can be exemplified. For example, these measurement devices 9 may be provided downstream of the pressure applying device 3 in the sampling channel 2. In the present embodiment, the pressure gauge 9*a* and the liquid flow rate meter 9*b* may be provided as the measurement device 9, and the pressure gradient may be controlled based on both the flow pressure and the liquid flow speed. By doing so, the aseptic sampling apparatus 1 can control the pressure gradient more accurately.

Hereinafter, the present embodiment will be described more specifically with reference to FIG. 1. Cells are cultured in an aseptic state maintained under predetermined conditions for a long period of time. The cells are cultured by uniformly mixing and stirring the cell-suspended culture liquid 5 with a stirrer 10 in the culture tank 4 filled with a medium optimized for the cells.

Although not illustrated in FIG. 1, various existing sterilizable sensors are installed in the culture tank 4, so that the temperature, the pH, the dissolved oxygen (DO) concentration, and the like are analyzed and controlled by an appropriate means. For example, the DO concentration is controlled by ventilating the aseptic air (or mixed air of oxygen and aseptic air) into the liquid with the submerged ventilation means 6. As an example, FIG. 1 illustrates an example where microbubbles are generated by using the sparger 11 having micropores. When microbubbles have an effect such as inhibiting the cell culture, the membrane surface ventilation through a porous membrane is applied.

In addition, the control of proper pH of the culture liquid 5 is performed by ventilating the gas in which carbon dioxide is mixed with the aseptic air with the liquid surface ventilation means 7 or by adding an acid or an alkali with a liquid supply means (not illustrated). The amount of liquid supplied by the liquid supply means is controlled by the liquid feeding pump (not illustrated). It is noted that, the liquid supply means may be used as a means for supplying an added medium containing nutrients required for the cell culture during the culture.

In the culture state and quality control of the cells, when it is necessary to analyze the medium components or the cells themselves outside the culture system to monitor a metabolic reaction and the cell state of the cells, the culture liquid 5 containing the cells appropriately is fractionated into a plurality of sampling containers 12 from the culture tank 4 through the sampling channel 2 at regular quantities or at regular intervals by the pressure applying device 3 and sampled. As an example in FIG. 1, the predetermined amount of culture liquid 5 required for analysis is collected in the sampling containers 12 arranged in a fraction collector 13. The collected culture liquid 5 is manually or automatically introduced into the analysis device 14 to be applied to various analyses.

In the related art, in order to prevent contamination due to the indigenous bacteria in the room from the open-end nozzle 2*b* on the outlet side of the sampling channel 2, the open-end nozzle 2*b* needs to be sterilized with the steam, the flame, the disinfectant, or the like before and after the sampling. In addition, in the related art, the required amount is manually collected from the sampled culture liquid 5 and analyzed.

In the present embodiment, as the result of various studies on the length and flow speed of the sampling channel 2, the pressure gradient in the sampling channel 2 of the aseptic sampling apparatus 1 is controlled so as to be 1 kPa/m or more, preferably 100 kPa/m or less, more preferably, for example, 10 kPa/m to 30 kPa/m. By doing so, the aseptic sampling apparatus 1 can prevent contamination from the open-end nozzle 2*b* on the outlet side of the sampling channel 2 with a simple configuration and at low cost, and also enables continuous sampling.

It is noted that, the pressure loss Δp (Pa) of the fluid flowing through the tube 2*a* can be calculated by using the Darcy-Weisbach equation expressed in the following formula (1).

[Formula 1]

$$\Delta p = f\frac{L}{D}\frac{\rho V^2}{2} \tag{1}$$

Herein, in the formula (1),

L: length of the tube 2*a* (m)

D: inner diameter (m) of the tube 2*a*

V: average flow speed (m/s)

ρ: fluid density (kg/m$^3$)

f: friction loss coefficient (−)

It is noted that the friction loss coefficient f is expressed by the following formula (2) according to Hagen-Poiseuille's law in a laminar flow state.

$$f=64/\mathrm{Re} \tag{2}$$

Herein, in the formula (2), Re denotes a Reynolds number. For flows in circular tubes, a Reynolds number of 2,000 or more, for example, in the range of 2,300 to 4,000 is an index of turbulent transition. When the flow becomes a flow in the turbulent region in the sampling channel 2, there is a probability that damage to the cells can occur. For example, when an analysis target is human-derived or animal-derived cells or stem cells, since the cells have no cell wall unlike microorganism cells, the cells may be damaged by shear stress.

In the Darcy-Weisbach formula (1) described above, the pressure gradient Δp/L (Pa/m) indicating the pressure loss Δp (Pa) according to the length L (m) of the tube 2*a* depends on the inner diameter D (m) and the average flow speed V (m/s). FIG. 2 is a graph illustrating an example of selection of the inner diameter of the tube 2*a* for sampling and the flow rate. In FIG. 2, a relationship between the inner diameter of the tube 2*a* and the sampling flow rate for controlling the pressure gradient of the sampling channel 2 in the present embodiment to be 10 kPa/m to 30 kPa/m, which is a preferable range, is indicated by a thick solid line (left vertical axis). In addition, in FIG. 2, the calculated value of the Reynolds number Re at each sampling flow rate is indicated by a dashed line (right vertical axis).

As illustrated in FIG. 2, when the inner diameter of the tube 2*a* exceeds 1.5 mm, the Reynolds number Re becomes 2,000 or more. As described above, when the Reynolds number Re is 2,000 or more, the flow becomes a flow in the turbulent region. Therefore, in the aseptic sampling apparatus 1 according to the present embodiment, it is preferable that the inner diameter of the tube 2*a* of the sampling channel 2 is 1.5 mm or less. By doing so, since the flow speed when extracting the culture liquid 5 is in a laminar flow region with the Reynolds number of less than 2,000, cells can be prevented from being damaged even when animal-derived cells are used.

It is noted that, in the present embodiment, the inner diameter of the tube 2*a* and the sampling flow rate are appropriately set according to each culture sampling liquid amount required for analysis by the analysis device 14. Since the required amount of liquid in the analysis device 14 is usually small, it is preferable to set the inner diameter of the tube 2*a* in the sampling channel 2 to about 0.1 mm to 0.5 mm. For example, when the inner diameter of the tube 2*a* is 0.5 mm, it is preferable that the sampling flow rate is 0.9 to 3.0 mL/min, as illustrated in FIG. 2.

The flow rate control in this case can be performed, for example, by measuring the flow rate (liquid flow speed) with the liquid flow rate meter 9*b* which is the measurement device 9 installed in the sampling channel 2 and appropriately controlling the output of the liquid feeding pump 3*a* which is the pressure applying device 3 based on the measured liquid flow speed. Accordingly, the above-described pressure gradient can be controlled.

In addition, the flow rate control can be performed by measuring the flow pressure with the pressure gauge 9*a* which is the measurement device 9 installed in the sampling channel 2 and appropriately controlling the output of the liquid feeding pump 3*a* which is the pressure applying device 3 based on the measured flow pressure. Accordingly, the above-described pressure gradient can be controlled. It is noted that, in this case, a target value of the control pressure of the pressure gauge 9*a* is set according to the length L of the tube 2*a* in the sampling channel 2. For example, when the length L of the tube 2*a* in the sampling channel 2 is set to 1 m, differential pressure Δp in the liquid feeding pump 3*a* with respect to the atmospheric pressure in the open-end nozzle 2*b* on the outlet side of the sampling channel 2 is 1 kPa or more, preferably 100 kPa or less, more preferably, for example, 10 kPa to 30 kPa. It is noted that, in the example illustrated in FIG. 1, the length L of the tube 2*a* corresponds to a length from the installation position of the pressure gauge 9*a* to the open-end nozzle 2*b* on the outlet side.

In addition, although the example of sampling using the liquid feeding pump 3*a* is illustrated in FIG. 1, when the culture tank 4 is made of glass or resin and has rigidity, the sampling flow rate of the culture liquid 5 in the sampling channel 2 may be controlled by increasing or decreasing a ventilation pressure or a flow rate of the gas aerated to the liquid surface of the culture tank 4 by the liquid surface ventilation means 7. In this case, the air pump, the air compressor, or the like (not illustrated) used in the liquid surface ventilation means 7 corresponds to the pressure applying device 3. By applying these means described above, the aseptic sampling apparatus 1 is capable of continuously sampling without contamination of the various germs from the open-end nozzle 2*b* on the outlet side.

Second Embodiment

FIG. 3 is a schematic diagram illustrating an overall configuration of a cell culture apparatus 30 including an aseptic sampling apparatus 1 according to a second embodiment.

As illustrated in FIG. 3, the aseptic sampling apparatus 1 according to the present embodiment is different from the aseptic sampling apparatus 1 according to the first embodiment, in terms that the sampling channel 2 is branched into two in the middle path, one open-end nozzle 2*c* on one outlet side is connected to the analysis device 14 via a valve Va, and the other open-end nozzle 2*d* on the outlet side is connected to a waste liquid container 15 via a valve Vb. The second embodiment is performed centering on the configuration different from the first embodiment. It is noted that, in the second embodiment, elements having already been described are denoted by the same reference numerals, and detailed description thereof may be omitted.

Depending on the analysis device 14, it may take a certain amount of time to perform the predetermined analysis step, and the sampled culture liquid 5 may not be continuously received and analyzed. Moreover, in some cases, depending on the purpose of culture, it is preferable that the analysis is performed at a certain time interval. Furthermore, in culturing with the cell culture apparatus 30, there is a case where the culture liquid 5 in the culture tank 4 is directly tested to the analysis device 14 to analyze the culture liquid 5 at an appropriate timing. The aseptic sampling apparatus 1 illustrated in FIG. 3 and the cell culture apparatus 30 provided with the same are invented to satisfy the demands.

As illustrated in FIG. 3, one open-end nozzle 2*c* of the sampling channel 2 branching into two is connected to the analysis device 14. For this reason, by opening the valve Va while applying pressure to the culture liquid 5 in the sampling channel 2 with the pressure applying device 3, the sampled culture liquid 5 can be tested in the analysis device 14. In addition, the other open-end nozzle 2*d* of the sampling channel 2 is connected to the waste liquid container 15. For this reason, by opening the valve Vb while applying pressure to the culture liquid 5 in the sampling channel 2 with the pressure applying device 3, the sampled culture liquid 5 that is not required for the analysis can be stored in the waste liquid container 15.

Therefore, for example, normally, an aspect can be used where, by closing the valve Va and opening the valve Vb, the sampled culture liquid 5 is stored in the waste liquid container 15, and by opening the valve Va and closing the valve Vb during the analysis, the sampled culture liquid 5 is tested to the analysis device 14.

When the liquid is stored in the waste liquid container 15 and when the liquid is fed to the analysis device 14, as described above, the fluid in the sampling channel 2 is controlled by the pressure applying device 3 so that the pressure gradient toward the open-end nozzle 2*c* the outlet side of the sampling channel 2 is 1 kPa/m or more, preferably 100 kPa/m or less, more preferably, for example, 10 kPa/m to 30 kPa/m. Therefore, the aseptic sampling apparatus 1 according to the present embodiment can prevent contamination due to the various germs from the open-end nozzle 2*d* on the outlet side arranged in the waste liquid container 15 and can maintain the asepticity in the culture tank 4. In addition, the aseptic sampling apparatus 1 according to the present embodiment can reliably feed the culture liquid 5 to the analysis device 14 while preventing contamination. Furthermore, the aseptic sampling apparatus 1 according to the present embodiment enables changing the settings of various control means controlling the culture in the cell culture apparatus 30, such as the stirrer 10, the submerged ventilation means 6, the liquid surface ventilation means 7, and the medium supply means 8 according to the analysis result by the analysis device 14. Therefore, the aseptic sampling apparatus 1 according to the present embodiment contributes to maintaining good culture states in the cell culture apparatus 30.

It is noted that, in the present embodiment, it is preferable that a portion of the tube 2*a* of the sampling channel 2 having an inner diameter of 1.5 mm or less be arranged immediately before the analysis device 14. In other words, it is preferable that the tube 2*a* having an inner diameter of 1.5 mm or less is connected to the analysis device 14. A lot of the analysis devices 14 can be connected to such a small-diameter tube 2*a*, and the sampled culture liquid 5 can be directly tested in the analysis device 14. In addition, when the inner diameter is 1.5 mm or less, since the flow rate of the culture liquid 5 is small, the used amount of the culture liquid 5 can be reduced.

Third Embodiment

FIG. 4 is a schematic diagram illustrating an overall configuration of a cell culture apparatus 30 including an aseptic sampling apparatus 1 according to a third embodiment.

In the first embodiment, although the example where the culture liquid 5 in the culture tank 4 is continuously sampled is illustrated, in the third embodiment illustrated in FIG. 4, the aseptic sampling is performed as appropriate at the timing when the analysis of the culture liquid 5 is required. For this reason, the aseptic sampling apparatus 1 according to the third embodiment discards the culture liquid 5 remaining in the sampling channel 2 with the fluid other than the culture liquid 5 so that the culture liquid 5 does not remain in the sampling channel 2. After that, the aseptic sampling apparatus 1 prevents contamination due to the various germs by continuously feeding-out (feeding) the fluid, preferably liquid, toward the open-end nozzle 2*b* on the outlet side of the sampling channel 2.

In order to implement the aseptic sampling apparatus 1, as illustrated in FIG. 4, the aseptic sampling apparatus 1 according to the third embodiment is different from the aseptic sampling apparatus 1 according to the first embodiment in terms of including the switching mechanism 16 in the sampling channel 2. The third embodiment is performed centering on the configuration different from the first Embodiment. It is noted that, in the third embodiment, elements having already been described are denoted by the same reference numerals, and detailed description thereof may be omitted.

Herein, the switching mechanism 16 switches between at least one fluid selected from an aseptic liquid 17, aseptic water 18, a buffer solution, and the aseptic air and the culture liquid 5. By doing so, contamination can be prevented more reliably. It is noted that, although the buffer solution is not illustrated, for example, the buffer solution can be used, for example, similarly to the aseptic water 18. Two or more of the aseptic liquid 17, the aseptic water 18, the buffer solution, and the aseptic air can be used as illustrated in FIG. 4 (FIG. 4 illustrate a case of using two elements).

Herein, the aseptic liquid 17 denotes a solution containing components for sterilizing bacteria. As the aseptic liquid 17, for example, 60 to 70% alcohol, sodium hypochlorite aqueous solution, hypochlorous acid water, and the like can be exemplified.

The aseptic water 18 denotes sterilized water. The aseptic water 18 can be sterilized by, for example, an autoclave at about 121° C.×30 to 60 minutes or the filtration or the like.

The buffer solution is an aqueous solution in which the pH does not change significantly even if the small amount of acid or base is added or a concentration is slightly changed. As the buffer solution, for example, phosphate buffered physiological saline solution, a tris buffer solution, a citrate phosphate buffer solution, a citrate buffer solution, a phosphate buffer solution, an acetate buffer solution, and the like can be exemplified. The buffer solution after being sterilized as described above can also be used.

The aseptic air denotes the air or oxygen filtered by an aseptic air ventilation means 19 having the aseptic filter F to remove the various germs and the like. That is, the aseptic air is supplied by the aseptic air ventilation means 19. It is noted that oxygen can be supplied from an oxygen tank or the like through the aseptic filter and can be mixed with air (aseptic air) as described above, if necessary.

The aseptic filter F is also provided in a storage tank for the aseptic liquid 17 and a storage tank for the aseptic water 18. Accordingly, the asepticity can be maintained even when these tanks take in outside air.

During the sampling, the aseptic sampling apparatus 1 switches by the switching mechanism 16 to feed the culture liquid 5 toward the open-end nozzle 2*b* on the outlet side of the sampling channel 2. Then, at the time of other than the sampling, being switched by the switching mechanism 16, the aseptic sampling apparatus 1 feeds out at least one of the aseptic liquid 17, the aseptic water 18, the buffer solution, and the aseptic air toward the open-end nozzle 2*b* on the outlet side of the sampling channel 2. Thus, the aseptic sampling apparatus 1 includes the switching mechanism 16, so that the culture liquid 5 can be fed only during the sampling. For this reason, the aseptic sampling apparatus 1 can reduce an amount of the culture liquid 5 extracted from the culture tank 4.

The switching mechanism 16 may not be limited to a specific configuration as long as the switching mechanism can switch between the aseptic liquid 17 and the like and the culture liquid 5, but for example, the switching mechanism can suitably switch as follows.

As illustrated in FIG. 4, the culture tank 4 is filled with the culture liquid 5 containing cells, and similarly to the first embodiment, while ventilation and stirring are performed by the submerged ventilation means 6 and the liquid surface ventilation means 7, the target cells are cultured as usual by performing the control of the culture temperature, the DO, the pH, and the like. It is noted that, although not illustrated in FIG. 4, the culture tank 4 may be provided with the medium supply means 8 and the liquid feeding pump 3*b*. Whether or not the culture tank 4 includes the submerged ventilation means 6, the liquid surface ventilation means 7, the medium supply means 8, and the liquid feeding pump 3*b* varies depending on a culture method and the cells, so that these elements can be freely set, if necessary. As the culture method, batch culture, fed-batch culture, perfusion culture, and the like can be exemplified in terms of the addition timing of the liquid medium, and static culture, ventilation culture, stirring culture, shaking culture, and the like can be exemplified in terms of the stirring method.

Valves V1 to V7 in FIG. 4 are electromagnetic valves or pinch valves of which opening/closing drive can be controlled by the control device (not illustrated). When the tube and the like are flexible, in the pinch valve that opens and closes the channel by pinching the tube, the liquid does not flow inside a valve body, so liquid pooling does not occur, and thus, it is easy and preferable to exchange the tube. For this reason, in the present embodiment, it is preferable that all the tubes including the sampling channel 2 are made of flexible resin. In addition, in the present embodiment, a tube operating mechanism 20 capable of freely moving the position of the open-end nozzle 2*b* on the outlet side of the sampling channel 2 is provided.

In the initial stage of start of the cell culture, the open-end nozzle 2*b* on the outlet side of the sampling channel 2 is arranged in the waste liquid container 15 by the tube operating mechanism 20, and the aseptic water 18 is continuously fed to the sampling channel 2. Therefore, in the initial stage of the start of the cell culture, the valves V1, V4, and V6 are closed, and the valves V2, V3, V5, and V7 are opened. The liquid flow rate of the aseptic water 18 is measured by the liquid flow rate meter 9*b*, and the output of a liquid feeding pump 3*d* is controlled based on the measured value. As illustrated in FIG. 2, the flow rate of the aseptic water 18 at this time may be set and controlled according to the inner diameter of the tube 2*a* in the sampling channel 2.

Then, when necessarily sampling and analyzing the culture liquid 5, the aseptic sampling is performed according to the following operation flow.

(1) The valves V5 and V7 are closed from the initial state of the start of the cell culture described above. That is, the valves V1, V4, V5, V6, and V7 are closed, and the valves V2 and V3 are opened. In addition, along with this valve operation, the liquid feeding pump 3*d* is stopped.

(2) Next, the valve V4 is opened. That is, the valves V1, V5, V6, and V7 are closed, and the valves V2, V3, and V4 are opened. As a result, the aseptic air ventilation means 19 ventilates the aseptic air into the sampling channel 2, and the liquid remaining in the sampling channel 2 can be discarded in the waste liquid container 15. As illustrated in FIG. 2, it is preferable that the flow rate of the aseptic air at this time is also set and controlled according to the inner diameter of the tube 2*a* in the sampling channel 2. In addition, it is preferable that, similarly to other fluids, the aseptic air is also controlled so that the pressure gradient of the aseptic air toward the open-end nozzle 2*b* on the outlet side of the sampling channel 2 is 1 kPa/m or more.

(3) Next, the valve V4 is closed. That is, the valves V1, V4, V5, V6, and V7 are closed, and the valves V2 and V3 are opened. In addition, the tube operating mechanism 20 moves the open-end nozzle 2*b* on the outlet side of the sampling channel 2 to the sampling container 12.

(4) Then, the valve V1 is opened. That is, the valves V4, V5, V6, and V7 are closed, and the valves V1, V2, and V3 are opened. In this state, the required amount of the culture liquid 5 is sampled from the culture tank 4. At this time, the liquid surface ventilation means 7 adjusts the pressure of the aseptic air that is ventilated to the gas phase portion of the culture tank 4, so that the differential pressure corresponding to the length of the sampling channel 2 from the culture tank 4 to the open-end nozzle 2*b* is set. The flow rate of the culture liquid 5 at this time is also set and controlled according to the inner diameter of the tube 2*a* in the sampling channel 2 as illustrated in FIG. 2. The liquid flow rate can also be measured by the liquid flow rate meter 9*b* and controlled based on the result. In addition, the culture liquid 5 is controlled so that the pressure gradient toward the open-end nozzle 2*b* on the outlet side of the sampling channel 2 is 1 kPa/m or more.

(5) The valve V2 is closed when the required amount of sampling is completed. That is, the valves V2, V4, V5, V6, and V7 are closed, and the valves V1 and V3 are opened. In addition, the tube operating mechanism 20 moves the open-end nozzle 2*b* on the outlet side of the sampling channel 2 to the waste liquid container 15.

(6) Then, the valve V4 is opened. That is, the valves V2, V5, V6, and V7 are closed, and the valves V1, V3, and V4 are opened. As a result, the aseptic air ventilation means 19 ventilates the aseptic air into the tube 2*a*, and the culture liquid 5 remaining in the tube between the culture tank 4 and the valve V1 can be returned to the culture tank 4.

(7) Next, the valves V1 and V4 are closed, and the valves V2, V5, and V6 are opened. That is, the valves V1, V4, and V7 are closed, and the valves V2, V3, V5, and V6 are opened. As a result, a liquid feeding pump 3*c* can feed the aseptic liquid 17 into the tube 2*a*. It is noted that the aseptic liquid 17 having been fed is discarded in the waste liquid container 15. It is preferable that the flow rate of the aseptic liquid 17 at this time is also set and controlled according to the inner diameter of the tube 2*a* in the sampling channel 2 as illustrated in FIG. 2. In addition, the aseptic liquid 17 is controlled so that the pressure gradient toward the open-end nozzle 2*b* on the outlet side of the sampling channel 2 is 1 kPa/m or more.

(8) After that, the valve V6 is closed, and the valve V7 is opened. That is, the valves V1, V4, and V6 are closed, and the valves V2, V3, V5, and V7 are opened. Accordingly, the liquid feeding pump 3*d* can continuously feed the aseptic water 18 into the tube 2*a*. It is noted that the aseptic water 18 having been fed is discarded into the waste liquid container 15. The flow rate of the aseptic water 18 at this time is set and controlled according to the inner diameter of the tube 2*a* in the sampling channel 2 as illustrated in FIG. 2. In addition, the aseptic water 18 is controlled so that the pressure gradient toward the open-end nozzle 2*b* on the outlet side of the sampling channel 2 is 1 kPa/m or more.

(9) Next, the valves V5 and V7 are closed, and the valve V4 is opened. That is, the valves V1, V5, V6, and V7 are closed, and the valves V2, V3, and V4 are opened. As a result, the aseptic air ventilation means 19 ventilates the aseptic air into the tube 2*a*, and the remaining liquid in the tube 2*a* can be discarded in the waste liquid container 15.

(10) After that, the valve V4 is closed, the valve V5 is opened, and the valve V6 or V7 is opened. That is, the valves V1 and V4 are closed, and the valves V2, V3, and V5 and one of the valves V6 and V7 are opened (in this case, the other of the valves V6 and V7 is closed). As a result, the aseptic liquid 17 or the aseptic water 18 is continuously fed into the sampling channel 2, and the aseptic state of the sampling channel 2 after the valve V3 is maintained. The flow rate of the aseptic liquid 17 or the aseptic water 18 at this time is also set and controlled according to the inner diameter of the tube 2*a* in the sampling channel 2 as illustrated in FIG. 2. In addition, the aseptic liquid 17 or the aseptic water 18 is controlled so that the pressure gradient toward the open-end nozzle 2*b* on the outlet side of the sampling channel 2 is 1 kPa/m or more. When the aseptic liquid 17 is fed out, the aseptic state of the sampling channel 2 after the valve V3 can be more reliably maintained. It is noted that, in this case, it is preferable that, when the next sampling step is performed, the above-described step (8) is performed, and after the aseptic water 18 is continuously fed into the tube 2*a*, the steps after the above-described step (1) are performed.

In the present embodiment, the culture liquid 5 can be aseptically sampled by the above-described operations.

Since the fluid such as the aseptic liquid 17 and the aseptic water 18 in the sampling channel 2 is controlled (the flow pressure or the flow speed is maintained and controlled) by the pressure applying device 3 so that the pressure gradient toward the outlet-side open-end nozzle 2*b* is 1 kPa/m or more, preferably 100 kPa/m or less, more preferably, for example, 10 kPa/m to 30 kPa/m, the simple and inexpensive configuration can maintain the asepticity (can prevent the contamination due to the various germs from the open-end nozzle 2*b* on the outlet side of the sampling channel 2) until the next sampling. In addition, during the sampling, the culture liquid 5 which is a fluid in the sampling channel 2 is controlled (the flow pressure or the flow rate is maintained and controlled) by the pressure applying device 3 so that the pressure gradient toward the open-end nozzle 2*b* on the outlet side is 1 kPa/m or more, preferably 100 kPa/m or less, more preferably, for example, 10 kPa/m to 30 kPa/m, so that the asepticity can be maintained.

Moreover, as illustrated in FIG. 4, it is preferable that the aseptic sampling apparatus 1 according to the third embodiment includes a check valve 21 in the sampling channel 2. By including the check valve 21 in this manner, the aseptic sampling apparatus 1 can prevent a backflow of the culture liquid 5 or the like in the sampling channel 2. Therefore, even if any instrument provided in the cell culture apparatus 30 malfunctions or an operation error occurs, the culture tank 4 can be prevented from being contaminated due to the backflow of the culture liquid 5 contaminated due to the various germs through the sampling channel 2. The check valve 21 is installed at any position, but the installation position is preferably downstream of the measurement device 9. By doing so, the culture liquid 5 contaminated due to the various germs can be prevented from contaminating the measurement device 9. Needless to say, the check valve 21 can be provided in the sampling channel 2 in the first and second embodiments as well.

It is noted that, in the present embodiments described above, the aseptic water 18 is continuously fed to the sampling channel 2 in the initial stage of the start of the cell culture. In contrast, the present embodiment can be modified as follows.

As the modified example, instead of the aseptic water 18, the aseptic liquid 17 may be fed to the sampling channel 2. In the modified example, the valves V1, V4, and V7 are closed, and the valves V2, V3, V5, and V6 are opened. In addition, the liquid flow rate of the aseptic liquid 17 is measured by the liquid flow rate meter 9*b*, and the output of the liquid feeding pump 3*c* is controlled based on the measured value so that the pressure gradient of the aseptic liquid 17 is 1 kPa/m or more. When sampling the culture liquid 5, the inside of the sampling channel 2 may be rinsed with the aseptic water 18 immediately before sampling, if necessary. The rinsing with the aseptic water 18 can be performed by closing the valves V1, V4, and V6 and opening the valves V2, V3, V5, and V7.

In addition, as another modified example, instead of the aseptic water 18, the aseptic air may be ventilated through the sampling channel 2. In the modified example, the valves V1, V5, V6, and V7 are closed, and the valves V2, V3, and V4 are opened. In addition, a feeding flow rate of the aseptic air is measured by the pressure gauge 9*a*, and the output of the aseptic air ventilation means 19 can be controlled based on the measured value so that the pressure gradient of the aseptic air is 1 kPa/m or more.

In any of these modified examples, since the pressure gradient of the fluid is controlled so as to be 1 kPa/m or more, the asepticity can be maintained in the initial stage of the start of the cell culture (contamination due to the various germs can be prevented).

[Aseptic Sampling Method]

Next, an aseptic sampling method (hereinafter sometimes abbreviated as "the present method") according to the present embodiment will be described. It is noted that, in describing the present method, elements having already been described are denoted by the same reference numerals, and detailed description may be omitted.

The present method is an aseptic sampling method using the aseptic sampling apparatus 1 having the sampling channel 2 and the pressure applying device 3 described above. In the present method, the pressure applying device 3 described above controls the fluid in the sampling channel 2 so that the pressure gradient is 1 kPa/m or more toward the open-end nozzle 2*b* on the outlet side of the sampling channel 2. Therefore, in the present method, as described above, since the pressure gradient of the fluid in the sampling channel 2 is sufficiently high, the various germs cannot invade from the open-end nozzle 2*b* on the outlet side of the sampling channel 2. Therefore, the present method can prevent contamination from the open-end nozzle 2*b*. In other words, in the present method, the aseptic sampling apparatus 1 does not need to be provided with various devices for sterilizing the open-ended nozzle 2*b* with the steam, the flame, the disinfectant, or the like. In this manner, the present method can perform the aseptic sampling with a simple configuration and at low cost.

In addition, in the present method, it is preferable that, after sampling by feeding the culture liquid 5 into the sampling channel 2, at least one of the aseptic liquid 17, the aseptic water 18, and the buffer solution is switched to the culture liquid 5 and fed. This switching can be performed by the switching mechanism 16 described above. By doing so, since the culture liquid 5 can be fed only during the sampling, the amount of the culture liquid 5 extracted from the culture tank 4 can be reduced.

Heretofore, although the aseptic sampling apparatus 1 and the aseptic sampling method according to the invention have been described above in detail with reference to the embodiments, the spirit of the invention is not limited to these, and includes various modified examples. For example, the above-described embodiments have been described in detail in order to explain the invention in an easy-to-understand manner, and the invention is not necessarily limited to those having all the described configurations. In addition, a portion of a configuration of one embodiment can be replaced with a configuration of another embodiment, and the configuration of another embodiment can be added to the configuration of one embodiment. Moreover, it is possible to add, delete, or replace a portion of the configuration of each embodiment with another configuration.

REFERENCE SIGNS LIST

1: aseptic sampling apparatus
2: sampling channel
2*a*: tube
2*b*, 2*c*, 2*d*: open-end nozzles
3: pressure applying device
4: culture tank
5: culture liquid
6: submerged ventilation means
6*a*: tube
7: liquid surface ventilation means
7*a*: tube

8: medium supply means
8*a*: tube
9: measurement device
9*a*: pressure gauge
9*b*: liquid flow rate meter
10: stirrer
11: sparger
12: sampling container
13: fraction collector
14: analysis device
15: waste liquid container
16: switching mechanism
17: aseptic liquid
18: aseptic water
19: aseptic air ventilation means
20: tube operating mechanism
21: check valve
30: cell culture apparatus
V1 to V7, Va, Vb: valves

The invention claimed is:

1. An aseptic sampling apparatus comprising:

a sampling channel extracting a culture liquid in a culture tank to be tested in an analysis device; and a pressure applying device applying pressure to the sampling channel, wherein the pressure applying device controls a fluid in the sampling channel so that a pressure gradient toward an open-end nozzle on an outlet side of the sampling channel is 1 kPa/m or more.

2. The aseptic sampling apparatus according to claim 1, wherein an inner diameter of a tube arranged in the sampling channel is 1.5 mm or less.

3. The aseptic sampling apparatus according to claim 2, wherein a material of the tube is fluororesin, polytetrafluoroethylene, tetrafluoroethylene/ethylene copolymer, tetrafluoroethylene/perfluoroalkyl vinyl ether copolymer, polyetheretherketone, or polyetheretherketone ketone.

4. The aseptic sampling apparatus according to claim 1, further comprising a measurement device measuring a flow pressure or a liquid flow speed in the sampling channel, wherein the pressure applying device is controlled based on a measured value measured by the measurement device, and the flow pressure or the liquid flow speed is controlled so as to achieve the pressure gradient.

5. The aseptic sampling apparatus according to claim 1, wherein the sampling channel is provided with a switching mechanism switching between at least one of an aseptic liquid, aseptic water, buffer solution, and aseptic air and the culture liquid.

6. The aseptic sampling apparatus according to claim 2, wherein the tube is arranged immediately before the analysis device.

7. The aseptic sampling apparatus according to claim 1, wherein the sampling channel includes a check valve.

8. The aseptic sampling apparatus according to claim 1, wherein a flow speed when extracting the culture liquid is in a laminar flow region with a Reynolds number of less than 2,000.

9. The aseptic sampling apparatus according to claim 1, wherein the pressure applying device is at least one of a tube pump, a diaphragm pump, an air pump for feeding aseptic air, and an air compressor for feeding aseptic air.

10. The aseptic sampling apparatus according to claim 1, wherein the pressure gradient is between 10 kPa/m and 30 kPa/m.

11. An aseptic sampling method using an aseptic sampling apparatus including a sampling channel extracting a culture liquid in a culture tank to be tested in an analysis device and a pressure applying device applying pressure to the sampling channel, the method comprising:

controlling a fluid in the sampling channel so that the pressure gradient toward an open-end nozzle on an outlet side of the sampling channel is 1 kPa/m or more, by the pressure applying device.

12. The aseptic sampling method according to claim 11, wherein, after sampling by feeding the culture liquid into the sampling channel, at least one of aseptic liquid, aseptic water, and buffer solution is switched to the culture liquid and fed.

13. The aseptic sampling method according to claim 11, wherein the pressure gradient is between 10 kPa/m and 30 kPa/m.

* * * * *